United States Patent

Shimshock et al.

[11] Patent Number: 6,100,276
[45] Date of Patent: Aug. 8, 2000

[54] ISATIN DERIVATIVES AS ACETYLCHOLINESTERASE INHIBITORS AND ANALGESICS

[75] Inventors: Stephen J. Shimshock, Somerville; Susan M. Chesson, Branchburg, both of N.J.; Abdul E. Mutlib, Bear, Del.

[73] Assignee: Aventis Pharmaceuticals Inc., Bridgewater, N.J.

[21] Appl. No.: 08/806,012

[22] Filed: Feb. 24, 1997

Related U.S. Application Data

[60] Provisional application No. 60/112,005, Apr. 12, 1996.

[51] Int. Cl.[7] ............... C07D 217/12; C07D 401/04; A61K 31/4709; A61K 31/44
[52] U.S. Cl. ............... 514/307; 514/339; 546/144; 546/146; 546/277.7
[58] Field of Search .................. 546/277.7, 144, 546/146; 514/339, 307

[56] References Cited

U.S. PATENT DOCUMENTS

| | | | |
|---|---|---|---|
| 4,970,218 | 11/1990 | Effland et al. | 514/339 |
| 4,999,358 | 3/1991 | Martin et al. | 514/297 |
| 5,006,537 | 4/1991 | Effland et al. | 514/339 |
| 5,053,511 | 10/1991 | Effland et al. | 514/278 |
| 5,179,099 | 1/1993 | Effland et al. | 514/278 |
| 5,179,119 | 1/1993 | Effland et al. | 514/409 |
| 5,296,488 | 3/1994 | Effland et al. | 514/278 |
| 5,464,846 | 11/1995 | Effland et al. | 514/333 |

FOREIGN PATENT DOCUMENTS

| | | |
|---|---|---|
| 0413191 | 2/1991 | European Pat. Off. . |
| 0415102 | 3/1991 | European Pat. Off. . |
| 0415103 | 3/1991 | European Pat. Off. . |

OTHER PUBLICATIONS

Ohnuma, Takeshi, et al. *Heterocycles*, vol. 17, 1982 pp. 377–380.
Davis, et al., *J. Med. Chem.*, 1996, vol. 39, pp. 582–587.
*Chem Abst.*, vol. 99, No. 53536(e), 1983, Berdinskii et al.
*Chem Abst.*, vol. 102, No. 95494, 1984.

*Primary Examiner*—Alan L. Rotman
*Attorney, Agent, or Firm*—Balaram Gupta

[57] ABSTRACT

This application relates to compounds of the formula

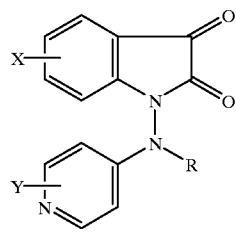

wherein R, X and Y are defined within, which compounds are useful for the treatment of memory dysfunction characterized by decreased cholinergic function, and for analgesia, pharmaceutical compositions containing the compounds and methods for making and using the compounds.

12 Claims, No Drawings

ISATIN DERIVATIVES AS ACETYLCHOLINESTERASE INHIBITORS AND ANALGESICS

This application claims the priority of U.S. Provisional application Ser. No. 60/112,005, filed Apr. 12, 1996.

This application relates to compounds of the formula

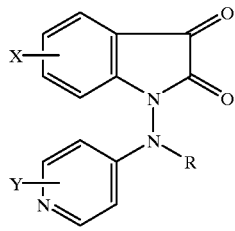

(I)

wherein $R^1$ is hydrogen, $(C_1-C_6)$alkyl or hydroxy $(C_1-C_6)$alkyl;

X is hydrogen, hydroxy, $(C_1-C_6)$alkoxy, phenyl$(C_1-C_6)$alkoxy, or —O(C=O)NR$^1$R$^2$; and Y is hydrogen or halogen;

where $R^1$ is $(C_1-C_6)$alkyl, phenyl, or phenyl$(C_1-C_6)$alkyl, where the phenyl group is optionally substituted by $(C_1-C_6)$alkyl, $(C_1-C_6)$alkoxy, halogen or trifluoromethyl;

$R^2$ is hydrogen or $(C_1-C_6)$alkyl; or $R^1$ and $R^2$ taken together with the nitrogen to which they are attached form a tetrahydroisoquinoline group; and its pharmaceutically acceptable acid addition salts;

which compounds are expected to be useful for inhibiting acetylcholinesterase and alleviating various memory dysfunctions characterized by decreased cholinergic function such as found in Alzheimer's disease.

This invention also provides a pharmaceutical composition useful for inhibiting acetylcholinesterase and alleviating various memory dysfunctions characterized by decreased cholinergic function which comprises a compound of the invention in an amount sufficient to effect cholinergic function and a pharmaceutically acceptable carrier. This invention further provides a method for alleviating the effects of Alzheimer's disease which comprises treating a patient with a pharmaceutically effective amount of a compound of the invention.

Unless otherwise stated or indicated, the following definitions shall apply throughout the specification and appended claims.

The term "alkyl" shall mean a straight or branched alkyl group of the stated number of carbon atoms. Examples include, but are not limited to methyl, ethyl, n-propyl, iso-propyl, n-butyl, isobutyl, sec-butyl, t-butyl, and straight and branched chain pentyl and hexyl.

The term "halo" shall mean chloro, fluoro, bromo and iodo.

The term "phenyl" shall mean phenyl having 0, 1, 2 or 3 substituents independently selected from the group of $(C_1-C_6)$alkyl, $(C_1-C_6)$alkoxy, halo or trifluoromethyl.

In a preferred embodiment of the invention are compounds of the Formula (I)

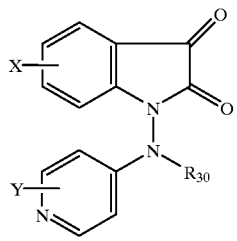

(I)

wherein

R is hydrogen, $(C_1-C_6)$alkyl or hydroxy$(C_1-C_6)$alkyl;

X is hydrogen, hydroxy, $(C_1-C_6)$alkoxy, benzyloxy, or —O(C=O)NR$^1$R$^2$; and Y is hydrogen or halogen;

where $R^1$ is $(C_1-C_6)$alkyl, phenethyl, or benzyl, where the phenyl group is optionally substituted by $(C_1-C_6)$alkyl, $(C_1-C_6)$alkoxy, halogen or trifluoromethyl; and $R^2$ is hydrogen or $(C_1-C_6)$alkyl; and its pharmaceutically acceptable acid addition salts.

More preferably when $R^1$ is $(C_1-C_6)$alkyl, $R^2$ is hydrogen.

In a preferred embodiment are compounds of Formula I wherein R is $(C_1-C_6)$alkyl.

More preferably X is hydrogen, Y is hydrogen and R is hydrogen, methyl, ethyl or propyl.

In an another preferred embodiment are compounds of Formula I

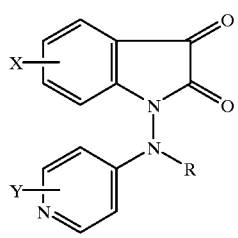

(I)

wherein

R is hydrogen, $(C_1-C_6)$alkyl or hydroxy$(C_1-C_6)$alkyl;

X is hydrogen, hydroxy, $(C_1-C_6)$alkoxy, benzyloxy, or —O(C=O)NR$^1$R$^2$; and Y is hydrogen or halogen; wherein $R^1$ and $R^2$ taken together with the nitrogen to which they are attached form a tetrahydroisoquinoline group; and its pharmaceutically acceptable acid addition salts.

Most preferably X is —O(C=O)NR$^1$R$^2$ and Y is hydrogen.

The compounds of the present invention may be prepared as shown in Scheme A wherein all substituents are as previously described.

Scheme A

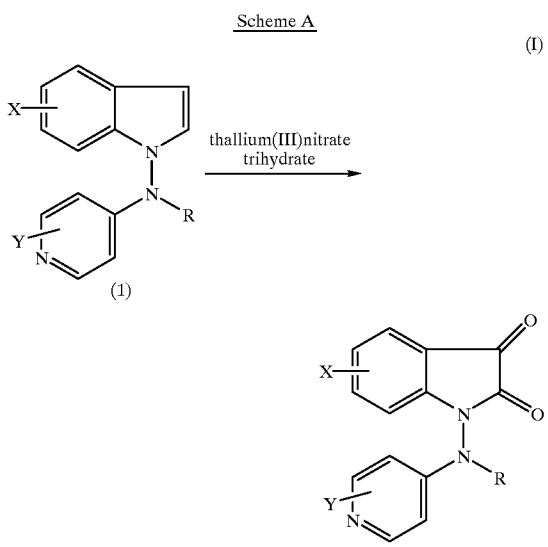

Scheme A provides a general synthetic procedure for preparing the compounds of formula (I).

The compounds of the invention are prepared by oxidation of the appropriate N-(pyridin-4-yl)-N-1H-indolyl-1-amine of structure (1) with a suitable oxidizing agent in a suitable organic solvent to give the corresponding 1-(pyridin-4-yl)-1H-indole-2,3-dione of formula (I). For example, the appropriate N-(pyridin-4-yl)-N-1H-indolyl-1-amine of structure (1) may be oxidized with thallium(III) trinitrate in methanol according to the procedure described in T. Ohnuma, et al., Heterocycles, 17, 377(1982). In addition, the appropriate N-(pyridin-4-yl)-N-1H-indolyl-1-amine of structure (1) may be oxidized with N-bromosuccinimide in a suitable organic solvent such as methylene chloride, chloroform, carbon tetrachloride or the like. These oxidations are carried out at temperatures ranging from about 0° C. to the reflux temperature of the solvent and the reaction time varies from about 1 hour to 72 hours, preferably from about 24 hours to about 72 hours.

The starting N-(pyridin-4-yl)-N-1H-indolyl-1-amines of structure (1) are known in the art or are prepared by procedures well known in the art. For example, the preparation of N-(pyridin-4-yl)-N-1H-indolyl-1-amines of structure (1) are described in U.S. Pat. No. 4,970,218 and by Davis et al. in J. Med. Chem., 39, pp 582 (1996).

The compounds of Formula I of the present invention can be used for the treatment of various memory dysfunctions characterized by decreased cholinergic function, such as Alzheimer's disease.

This utility can be demonstrated by determining by the ability of these compounds to inhibit the enzyme acetylcholinesterase and thereby increase acetylcholine levels in the brain.

The ability to inhibit acetylcholinesterase is determined by the photometric method of Ellman, et al., Biochem. Pharmacol. 7, 88 (1961).

This utility can also be ascertained by determining the ability of these compounds to restore cholinergically deficient memory in the Dark Avoidance Assay (Effland et. al., U.S. Pat. No. 5,053,511, issued Oct. 1, 1991). In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compounds, resulting in a greater interval before re-entry into the dark compartment.

The test results are expressed as the percent of a group of animals in which the effect of scopolamine is blocked, as manifested by an increased interval between being placed in the test chamber and re-entering the dark compartment.

Compounds of the present invention are useful as analgesic agents due to their ability to alleviate pain in mammals. The activity of the compounds can be demonstrated in the phenyl-para-quinone writhing assay in mice, a standard assay for analgesia (Proc. Soc. Exptl. Biol. Med., 95, 729 (1957)). The analgesic effect is expressed as either the subcutaneous dose at which 50% of the phenyl-para-quinone induced writhing is inhibited in the animals, i.e., the $ED_{50}$ value, or as the % decrease in writhing at a given dose.

The analgesic relief of pain is achieved when the compounds of the invention are administered to a subject requiring such treatment at an effective oral, parenteral or intravenous dose of from 0.01 to 100 mg/kg of body weight per day. A preferred effective dose within this range is from about 10 to about 50 mg/kg of body weight per day. It is to be understood, however, that for any particular subject, specific dosage regimens should be adjusted according to the individual need and the professional judgment of the person administering or supervising the administration of the compound. It is further to be understood that the dosages set forth herein are examples only and that they do not, to any extent, limit the scope or practice of the invention.

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 5% to about 70% of the weight of the unit. The amount of active compound in such compositions is such that a suitable dosage will be obtained. Preferred compositions and preparations according to the present invention are prepared so that an oral dosage unit form contains between 1.0–200 milligrams of active compound.

The tablets, pills, capsules, troches and the like may also contain the following ingredients: a binder such as microcrystalline cellulose, gum tragacanth or gelatin; an excipient such as starch or lactose; a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above-type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants such as ascorbic acid or sodium bisulfite; chelating agents such as ethylenediaminetetraacetic acid; buffers such as acetates; citrates or phosphates and agents for the adjustment of tonicity such as sodium chloride or dextrose. The parenteral multiple dose vials may be of glass or plastic.

The following Table I and examples will further illustrate this invention but are not intended to limit it in any way. In Table I typical compounds of the instant invention are listed. Following Table I, representative illustrative preparations of compounds of the invention are described.

TABLE I

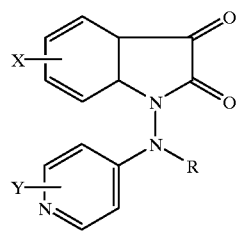

| Ex. No. | X | R | Y |
|---|---|---|---|
| 1 | H | CH$_2$CH$_2$CH$_3$ | H |
| 2 | H | H | H |

TABLE I-continued

| Ex. No. | X | R | Y |
|---|---|---|---|
| 3 | 5-OCH$_3$ | CH$_3$ | H |
| 4 | H | CH$_2$CH$_2$OH | 2'-Cl |
| 5 | 5-OC(=O)NHCH$_3$ | CH$_2$CH$_3$ | H |
| 6 | 5-OC(=O)N(CH$_3$)$_2$ | CH$_2$CH$_2$CH$_3$ | H |
| 7 | 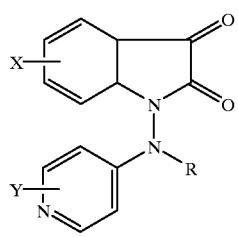 5-OC(=O)N | CH$_2$CH$_2$CH$_3$ | H |

EXAMPLE 1

1-(Propyl-pyridin-4-yl-amino)-1H-indole-2,3-dione

To a solution of N-propyl-N-(pyridin-4-yl)-N-1H-indolyl-1-amine (0.88 g, 3.50 mmol) in methanol (MeOH) (35 ml) there was added thallium(III) nitrate trihydrate (TTN) (2.4 g, 5.40 mmol) at room temperature. The reaction mixture was allowed to stir at room temperature under nitrogen for 72 hr, then filtered to remove a white precipitate. The filter cake was washed with MeOH and the filtrate was concentrated in vacuo to yield an oily solid (1.25 g). The oily solid was flash chromatographed (silica gel, MeOH/ethyl acetate, 0:10 to 20:80, yielded a solid, m.p. 132°–135° C. Spectral analysis was consistent with the expected product:

M.S. (EI, 70 ev)=281=M$^+$

IR (film) 1740 cm$^{-1}$ (s), shoulder at 1760 cm$^{-1}$

EXAMPLE 2

1-(Pyridin-4-yl-amino)-1H-indole-2,3-dione

To a solution of N-(pyridin-4-yl)-N-1H-indolyl-1-amine (0.10 g, 0.48 mmol) in methanol (MeOH) (10 ml) there is added thallium(III) nitrate trihydrate (TTN) (0.35 g, 0.79 mmol) at room temperature. The reaction mixture is allowed to stir at room temperature under nitrogen overnight, then filtered to remove a white precipitate. The filtrate is diluted with brine and extracted with ethyl acetate. The organic layer is dried (MgSO$_4$) concentrated in vacuo to yield an oil (0.15 g).

It should be understood that this specification and examples are set forth by way of illustration and not limitation and that various modifications and changes may be made without departing from the spirit and scope of the present invention as defined by the appended claims.

What is claimed is:

1. A compound of the formula

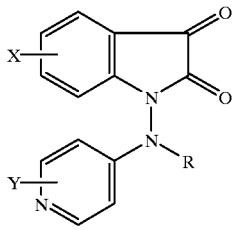

(I)

wherein
R is hydrogen, $(C_1-C_6)$alkyl or hydroxy $(C_1-C_6)$alkyl;
X is hydrogen, hydroxy, $(C_1-C_6)$alkoxy, phenyl$(C_1-C_6)$alkoxy, or —O(C=O)NR$^1$R$^2$; and
Y is hydrogen or halogen;
where R$^1$ is $(C_1-C_6)$alkyl, phenyl, or phenyl$(C_1-C_6)$alkyl, where the phenyl group is optionally substituted by $(C_1-C_6)$alkyl, $(C_1-C_6)$alkoxy, halogen or trifluoromethyl;
R$^2$ is hydrogen or $(C_1-C_6)$alkyl; or
R$^1$ and R$^2$ taken together with the nitrogen to which they are attached form an tetrahydroisoquinoline group; or a pharmaceutically acceptable acid addition salt thereof.

2. The compound of claim 1 wherein
R is hydrogen, $(C_1-C_6)$alkyl or hydroxy$(C_1-C_6)$alkyl;
X is hydrogen, hydroxy, $(C_1-C_6)$alkoxy, benzyloxy, or —O(C=O)NR$^1$R$^2$; and
Y is hydrogen or halogen;
where R$^1$ is $(C_1-C_6)$alkyl, phenethyl, or benzyl, where the phenyl group is optionally substituted by $(C_1-C_6)$alkyl, $(C_1-C_6)$alkoxy, halogen or trifluoromethyl; and R$^2$ is hydrogen; or a pharmaceutically acceptable acid addition salt thereof.

3. The compound of claim 2 wherein R$^1$ is hydrogen and R$^2$ is $(C_1-C_6)$alkyl.

4. The compound of claim 2 wherein R is $(C_1-C_6)$alkyl.

5. The compound of claim 4 wherein X is hydrogen, Y is hydrogen and R is hydrogen, methyl, ethyl or propyl.

6. The compound of claim 4 which is 1-(propyl-pyridin-4-yl-amino)-1H-indole-2,3-dione.

7. The compound of claim 5 which is 1-(pyridin-4-yl-amino)-1H-indole-2,3-dione.

8. The compound of claim 1 wherein
R is hydrogen, $(C_1-C_6)$alkyl or hydroxy$(C_1-C_6)$alkyl;
X is hydrogen, hydroxy, $(C_1-C_6)$alkoxy, benzyloxy, or —O(C=O)NR$^1$R$^2$; and
Y is hydrogen or halogen; wherein
R$^1$ and R$^2$ taken together with the nitrogen to which they are attached form an tetrahdyroisoquinoline group; or a pharmaceutically acceptable acid addition salt thereof.

9. The compound of claim 8 wherein X is OC(=O)NR$^1$R$^2$ and Y is hydrogen.

10. A pharmaceutical composition which comprises a pharmaceutically acceptable carrier and a pharmaceutically effective amount of the compound of claim 1.

11. A method for treating a patient in need of relief from a memory dysfunction characterized by decreased cholinergic function which comprises administering to such a patient an effective amount of the compound of claim 1.

12. A method for treating a patient in need of relief from pain which comprises administering to such a patient an effective amount of the compound of claim 1.

* * * * *